(12) United States Patent
Olfert (10) Patent No.: US 8,966,958 B2
(45) Date of Patent: Mar. 3, 2015

(54) PARTICLE CLASSIFIER

(75) Inventor: Jason Olfert, Edmonton (CA)

(73) Assignee: The Governors of the University of Alberta, Edmonton Alberta (CA)

( * ) Notice: Subject to any disclaimer, the term of this patent is extended or adjusted under 35 U.S.C. 154(b) by 310 days.

(21) Appl. No.: 13/379,627

(22) PCT Filed: Jul. 2, 2010

(86) PCT No.: PCT/CA2010/000995
§ 371 (c)(1),
(2), (4) Date: Dec. 20, 2011

(87) PCT Pub. No.: WO2011/000088
PCT Pub. Date: Jan. 6, 2011

(65) Prior Publication Data
US 2012/0096924 A1      Apr. 26, 2012

Related U.S. Application Data

(60) Provisional application No. 61/222,890, filed on Jul. 2, 2009.

(51) Int. Cl.
*G01N 15/10* (2006.01)
*G01N 15/12* (2006.01)
(Continued)

(52) U.S. Cl.
CPC .................................. *G01N 15/0255* (2013.01)
USPC ......... 73/28.04; 73/28.01; 73/28.05; 73/28.06

(58) Field of Classification Search
CPC . G01N 1/2273; G01N 15/02; G01N 15/1459; G01N 21/47; G01N 24/08; G01N 2015/1486; G01N 2015/149; G01N 2015/1493
USPC ......................... 73/28.01, 28.04, 28.05, 28.06
See application file for complete search history.

(56) References Cited

U.S. PATENT DOCUMENTS 3,429,187 A      2/1969  Stober
3,901,798 A  *   8/1975  Peterson ....................... 209/143
(Continued)

FOREIGN PATENT DOCUMENTS

| GB | 2416913 A  | 2/2006 |
| JP | 02-237657  | 9/1990 |
| WO | 99/41588 A1 | 8/1999 |

OTHER PUBLICATIONS

Olfert et al., "The Experimental Transfer Function of the Couette Centrifugal Particle Mass Analyzer", Journal of Aerosol Science, No. 37, 2006, pp. 1840-1852.*
(Continued)

*Primary Examiner* — David A Rogers
(74) *Attorney, Agent, or Firm* — Pedersen and Company, PLLC; Ken J. Pedersen; Barbara S. Pedersen (57) ABSTRACT

A new installment classifies particles by their aerodynamic size This installment produces a truly monodisperse aerosol, and can produce very narrow distributions over a wide range of sizes Particles suspended in a fluid are classified by supplying particles into suspension in a carrier flow of a fluid and providing an acceleration to the flow at an angle to the velocity of the flow to cause the particles to follow trajectories determined by the acceleration and drag on the particles caused by the fluid The particles are then classified according to their trajectories The installment has a flow channel and a source of particles to supply particles into suspension in a carrier fluid in the flow channel A drive is connected to the flow channel at an angle to the flow of fluid through the carrier flow channel, and a classification system classifies the suspended particles according to their trajectories.

28 Claims, 5 Drawing Sheets

(51) Int. Cl.
*G01N 15/14* (2006.01)
*G01N 1/20* (2006.01)
*G01N 15/02* (2006.01)

(56) References Cited

U.S. PATENT DOCUMENTS

| | | | |
|---|---|---|---|
| 4,640,140 A | 2/1987 | Burghoffer et al. | |
| 4,801,310 A * | 1/1989 | Bielefeldt | 210/788 |
| 4,842,738 A | 6/1989 | Greenspan | |
| 5,428,220 A | 6/1995 | Ehara | |
| 5,882,530 A * | 3/1999 | Chase | 210/788 |
| 6,251,296 B1 * | 6/2001 | Conrad et al. | 210/806 |
| 6,281,972 B1 * | 8/2001 | Ebara et al. | 356/336 |
| 6,544,312 B2 * | 4/2003 | Mullinger et al. | 55/434 |
| 6,809,314 B2 * | 10/2004 | Yoshida et al. | 250/288 |
| 7,028,847 B2 * | 4/2006 | Chen et al. | 209/713 |
| 7,082,811 B2 * | 8/2006 | Marple et al. | 73/28.05 |
| 7,298,486 B2 * | 11/2007 | Wang et al. | 356/438 |
| 8,104,362 B2 * | 1/2012 | McFarland et al. | 73/863.21 |
| 8,301,396 B1 * | 10/2012 | Dhanijala et al. | 702/24 |
| 8,528,427 B2 * | 9/2013 | Vrane et al. | 73/865.5 |
| 2002/0007620 A1 * | 1/2002 | Mullinger et al. | 55/434 |
| 2002/0124664 A1 * | 9/2002 | Call et al. | 73/863.22 |
| 2002/0179499 A1 * | 12/2002 | Kenning et al. | 209/143 |
| 2003/0052281 A1 * | 3/2003 | Rader et al. | 250/461.1 |
| 2004/0238415 A1 * | 12/2004 | Chen et al. | 209/713 |
| 2005/0028616 A1 | 2/2005 | Marple et al. | |
| 2005/0058575 A1 * | 3/2005 | Ishikawa et al. | 422/83 |
| 2006/0162424 A1 * | 7/2006 | Shekarriz et al. | 73/28.06 |
| 2008/0108146 A1 * | 5/2008 | Jiang | 436/165 |

OTHER PUBLICATIONS

Fissan et al; Experimental Comparison of Four Differential Mobility Analyzers for Nanometer Aerosol Measurements; 1996; Aerosol Science and Technolgy, 24:1, 1-13.

Charles Hagwood; The DMA Transfer Functino With Brownian Motion A Trajectory/Monte-Carlo Approach; 1999, Aerosol Science and Technology, 30:1, 40-61.

Richard C. Flagan; Opposed Migration Aerosol Classifier (OMAC); 2004; Aerosol Science and Technology, 38: 890-899.

Stein et al; Evaluation of a New Aerodynamic Particle Sizer Spectrometer for Size Distribution Measurements of Solution Metered Dose Inhalers; 2003; Journal of Aerosol Medicine, vol. 16, No. 2, 107-119.

Sawyer et al; The Conifuge—A Size-Separating Sampling Device for Airborne Particles; J Science Instrum; vol. 27, Oct. 1950, ;272-276.

Ohmura et al; Particle Classification in Taylor Vortex Flow With an Axial Flow; 2005, Journal of Physics; Conference Series 14; 64-71.

Monig et al; Summary Abstract: Measurement of Deposited Masses by Means of a Spiral Centrifuge With Quartz Sensors; J.Vac,Sci. Technol, A1(2); Apr.-Jun. 1983;284-285.

European Search Report, Application No. 10793465.5, PCT/CA2010/000995, Applicant: The Governors of the University of Alberta, Apr. 25, 2014.

Japanese Examiner's Action in corresponding Japanese National Entry of PCT/CA2010/000995, including English translation, citing Japanese Patent Application 02-237657, mailed Nov. 19, 2013.

Stoeber et al., Size-Separating Precipitation of Aerosols in a Spinning Spiral Duct, Environmental Science & Technology, Dec. 1, 1969, pp. 1280-1296, vol. 3, No. 12, 1969, Department of Radiation Biology and Biophysics, University of Rochester, School of Medicine and Dentistry, Rochester, N.Y. 14620, available from ACS Publications.

Kotrappa et al., Design and Performance of the Lovelace Aerosol Particle Separator, The Review of Scientific Instruments, Aug. 1972, pp. 1106-1112, vol. 43, No. 8, Fission Product Inhalation Laboratories, Lovelace Foundation for Medical Education and Research, Albuquerque, New Mexico 87108, available from AIP Publishing.

* cited by examiner

PARTICLE CLASSIFIER

This application is a 371 National Entry Application of PCT/CA2010/000995, which has an international filing date of Jul. 2, 2010 and is entitled "Particle Classifier", and which claims benefit of U.S. Provisional Application Ser. No. 61/222,890, filed Jul. 2, 2009 and entitled "Aerodynamic Particle Classifier".

TECHNICAL FIELD

Aerosol particle classifiers.

BACKGROUND

Aerosol classifiers are used to produce a monodisperse aerosol, that is, they select a narrow range of particles from a larger distribution of particles. This method is used for many applications including; nano-particle generation, measuring distributions of particles in air, measuring the deposition of particles in filters and other devices, sampling ambient aerosols, and many others. These measurements are often done in research areas as diverse as: nano-technology, pharmaceutical research, health-effects studies, inhalation toxicology, bio-aerosol detection, filter testing, indoor-air quality studies, industrial hygiene, energy and combustion research, automotive emissions measurements, and atmospheric and climate-change research.

Currently, the most commonly used classifier is called the Differential Mobility Analyzer (DMA, Knutson and Whitby 1975). The DMA classifies particles based on their electrical mobility, that is, the motion of a charged particle in an electrostatic field. By controlling the electrostatic field and the flow between two cylinders the particles are classified by their electrical mobility, which is related to the number of electric charges on the particle and the drag experienced by the particle, which is a function of the particle's size and shape. For non-spherical particles an equivalent diameter, called the electrical mobility equivalent diameter is defined for these particles, which have the same electrical mobility of a spherical particle of the same size. To classify particles with this instrument an electric charge must be placed on these particles using charging methods such radioactive-source charge neutralizers or corona discharge. However, with all charging methods not a single charge is placed on each particle but rather a distribution of charges are placed on the population of particles. For example, particles may obtain one, two, three, or more positive charges; one, two, three, or more negative charges or no charge at all. The electrical mobility of the particles is a function of the number of charges on the particle and its drag. Therefore, a smaller particle with one charge will have the same electrical mobility as a larger particle with two charges. Thus, the aerosol sample that is classified by the DMA will not be truly monodisperse in terms of particle size, but rather it will have a mix of sizes corresponding to an integer number of charged particles. Techniques are used to minimize the number of charge states but the DMA can never produce a truly monodisperse aerosol. For some applications (like measuring size distributions) the error introduced by the charge distribution can be corrected using inversion techniques, but it can never be fully eliminated. In other applications and experiments, these extra particle sizes can degrade performance or skew results.

Another technique has been used to classify particles by their mass-to-charge ratio is an instrument called the Aerosol Particle Mass analyzer (APM; Ehara et al. 1996; Ehara 1995) or the Couette Centrifugal Particle Mass Analyzer (Couette CPMA; Rushton and Reavell 2004; Olfert and Collings 2005). With these instruments charged particles are classified between two rotating cylinders with electrostatic and centrifugal forces. A similar charging mechanism is applied to charge the particles. Therefore, particles of the same mass-to-charge ratio will be classified. For example, a particle with one charge will be classified at the same time as a particle with twice the mass and twice the number of charges. Therefore, the APM or Couette CPMA do not produce a truly monodisperse aerosol.

Other aerosol and particle instruments are based on measuring what is called the 'aerodynamic' diameter of the particle. The aerodynamic equivalent diameter is defined as the diameter of a spherical particle with a density of water that has the same terminal velocity as the actual particle. Instruments that measure the aerodynamic size of particles include various kinds of impactors (Marple et al., 1991; Keskinen et al., 1992), virtual impactors (Conner, 1966), and aerodynamic lenses (Liu et al., 1995a, 1995b). However, these methods only provide a means of dividing the aerosol sample in half, where particles larger than the cut-off point are classified in one direction (i.e., impacted onto the impaction plate) and particles smaller than the cut-off point continue with the flow. Often, several of these stages are stacked together to provide classification into several large bins. There is currently no instrument that classifies particles by their aerodynamic diameter and produces a monodisperse aerosol.

SUMMARY

The applicant has devised a new instrument, called the Aerodynamic Particle Classifier (APC) that provides classification of particles. In an embodiment, a method of classification of particles suspended in a fluid is provided comprising the steps of providing a carrier flow of a fluid, supplying particles into suspension in the carrier flow, providing an acceleration to the flow at an angle to the velocity of the flow to cause the particles to follow trajectories determined by the acceleration and drag on the particles caused by the fluid, and classifying the particles according to the trajectories of the particles. The particles may be classified for example by splitting a flow containing the particles or by detecting impacts of the particles on boundaries of a flow channel containing the flow.

The following are features any or all of which may be provided in combination with the above method of classification of particles: the fluid may be a gas such as air; the carrier fluid may be caused to rotate around an axis by the rotation of one or more conveying flow channels; the acceleration may be centripetal acceleration; the step of supplying particles into suspension in the carrier flow may comprise merging a flow of a fluid containing suspended particles into the carrier flow; the step of classifying particles according to the trajectory of the particles may comprise splitting the carrier flow into two or more flows; and the step of classifying the particles according to the trajectory of the particles may comprise supplying a surface at which particles may impact depending on their trajectory.

Also provided is an apparatus for classifying particles suspended in a fluid, the apparatus comprising: elements defining one or more carrier flow channels, a source of a carrier fluid flow into the carrier flow channel, a source of particles connected to supply the particles into suspension in the carrier fluid in the carrier flow channel, a drive connected to operate on the elements defining the carrier flow channel to supply an acceleration to the elements defining the flow channel at an angle to the flow of fluid through the carrier flow channel, and a classification system for classifying the suspended particles according to their trajectories.

The following are features all or any of which may be provided in combination with the above apparatus for classifying particles: the carrier fluid may be a gas; the carrier flow may be caused to flow through one or more flow channels caused to rotate around an axis: the flow channels may be sectors or the whole of an annular space defined by inner and outer walls which are surfaces of revolution around an axis close to the axis of rotation; the surfaces of revolution may be substantially cylindrical in shape; the drive may comprise a motor connected to cause rotation of the elements defining the carrier flow channel; the source of particles connected to supply the particles into suspension in the carrier fluid in the carrier flow channel or channels may comprise elements defining a suspension flow channel or channels which intersect the carrier flow channels, the suspension flow channels being capable of directing a fluid containing suspended particles into the carrier flow channels; the classification system may comprise elements defining a split of each of the carrier flow channels into two or more channels; the classification system may comprise a surface in each carrier flow channel at which particles suspended in fluid in the carrier flow channel may impact depending on their trajectory; and the surface may be an element defining or partially defining the carrier flow channel.

These and other aspects of the device and method are set out in the claims, which are incorporated here by reference.

BRIEF DESCRIPTION OF THE FIGURES

Embodiments will now be described with reference to the figures, in which like reference characters denote like elements, by way of example, and in which:

FIG. 5 is a schematic of an APC (not to scale) with a where $\rho_p$ is the true particle density, $\rho_0$ is unit density (1000 kg/m³), and $d_{ae}$ is the so-called aerodynamic diameter of the particle.

Using the chain rule and differentiating, the radial position of the particle can be found as a function of the axial position, $$r(z) = r_{in} \exp\left(\frac{\tau \omega^2 z}{u_z}\right), \quad (3)$$

where $r_{in}$ is the initial position of the particle when it enters the classifier.

Figure 1:
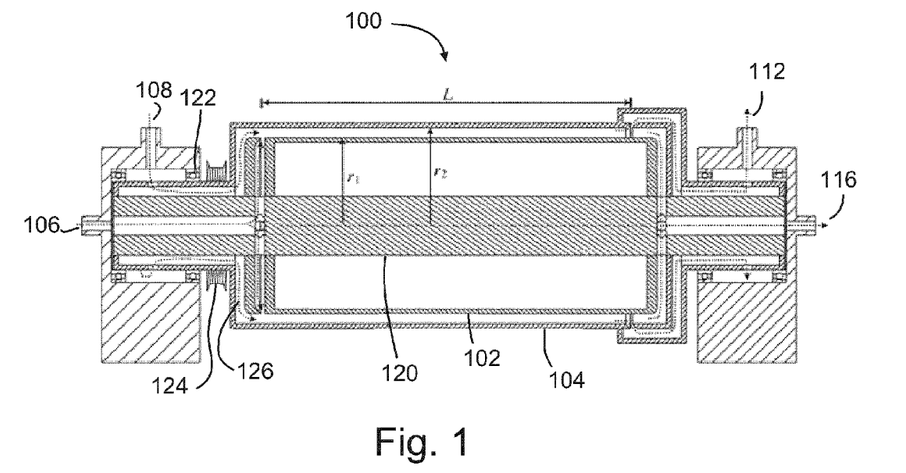
FIG. 1 is a schematic of an Aerosol Particle Classifier (APC) (not to scale) with a cylindrical flow path.
Figure 2:
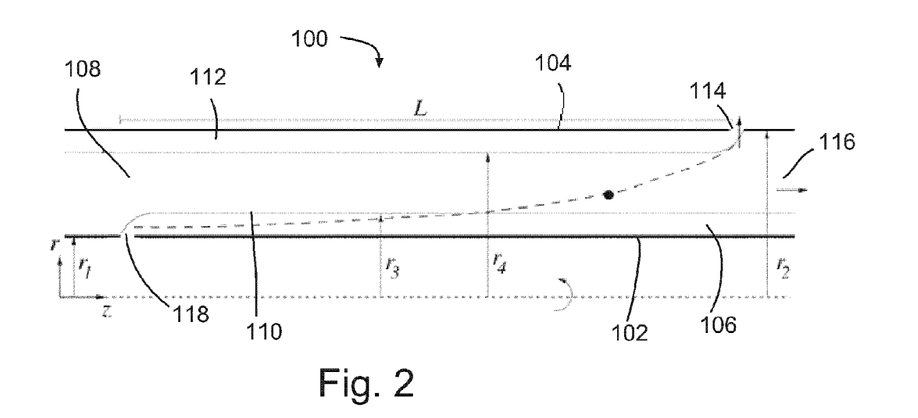
FIG. 2 is a diagram showing details of the particle trajectory and flows between the cylinders in the embodiment of FIG. 1.
Figure 3A:
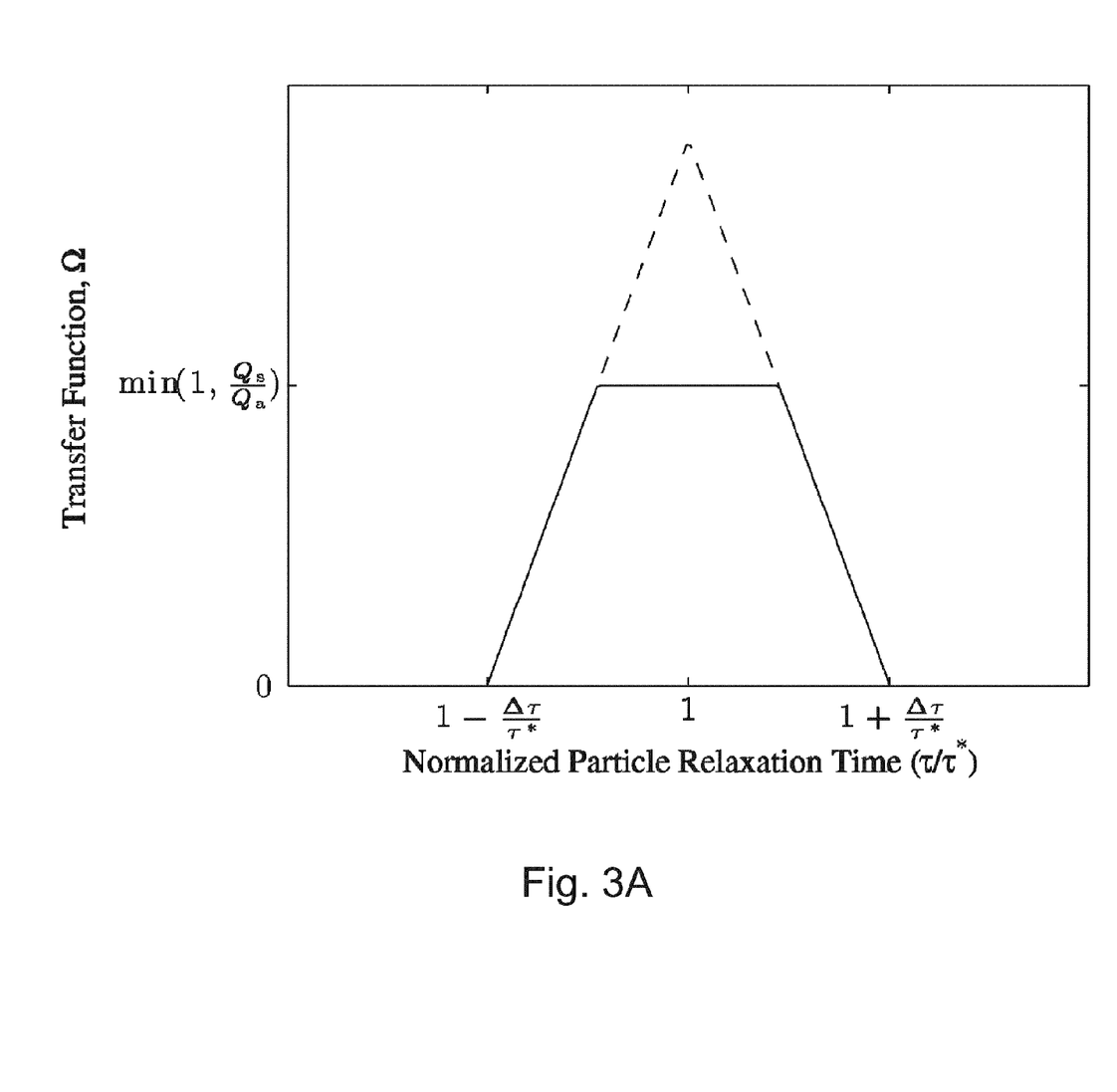
FIG. 3A is a graph of the normalized transfer function of the APC of FIG. 1.
Figure 3B:
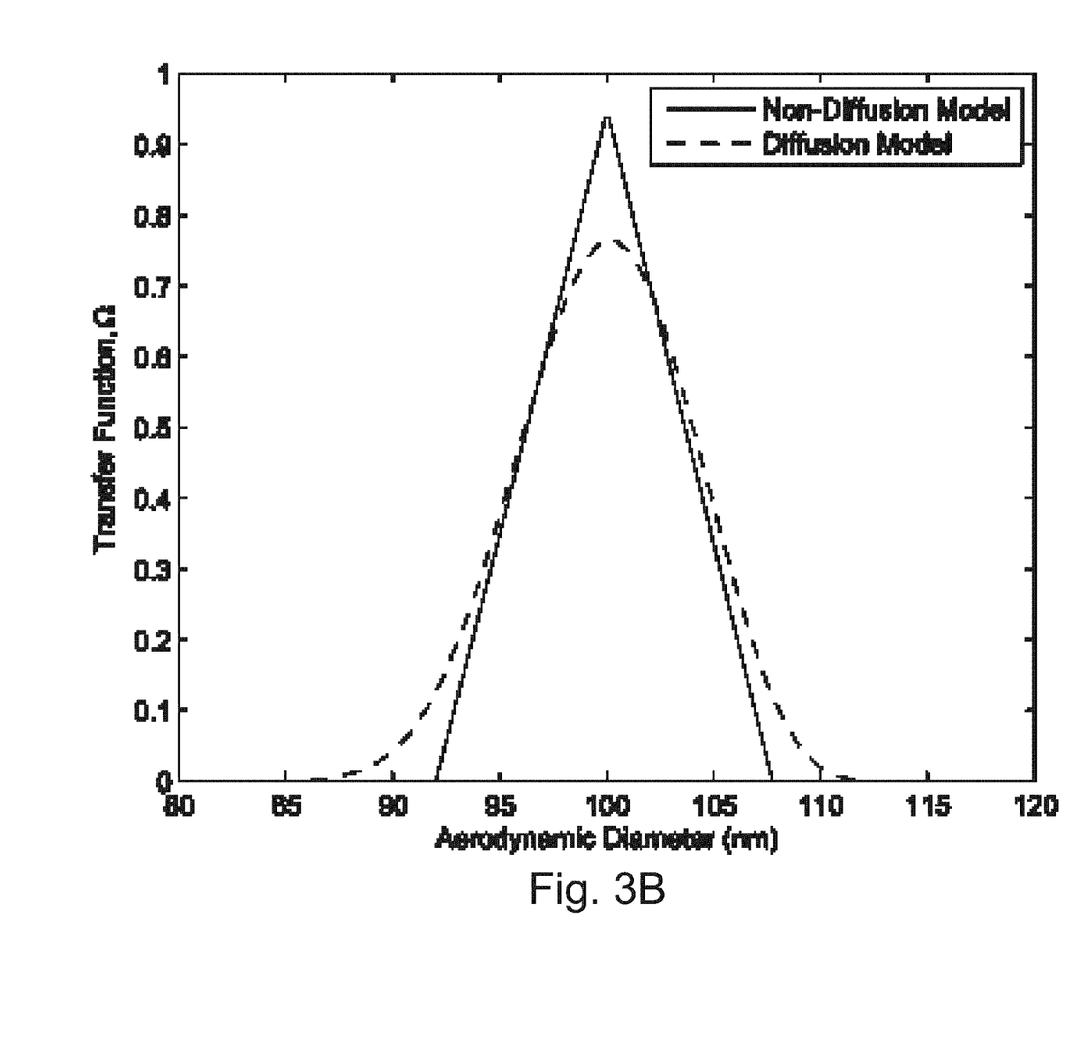
FIG. 3B is a graph of the transfer function of the APC of FIG. 1 in terms of aerodynamic diameter for the operating conditions given in the description.
Figure 4:
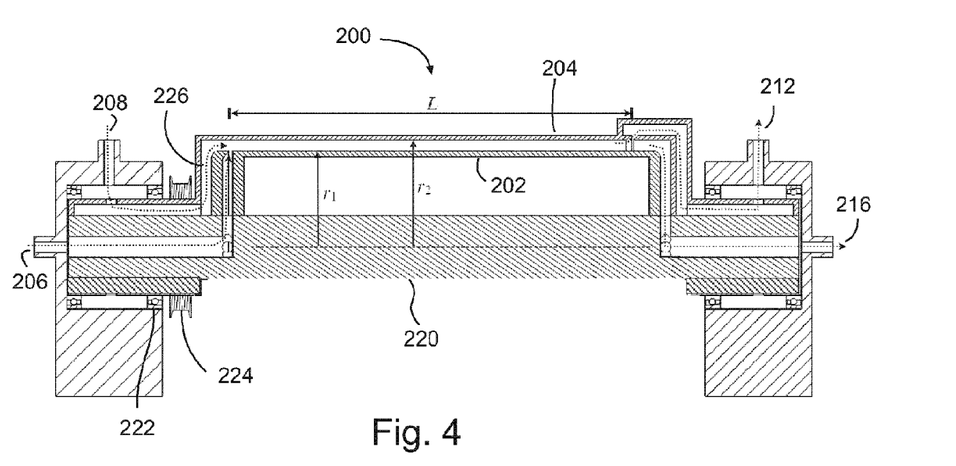
FIG. 4 is a schematic of an APC (not to scale) with a partial cylinder flow path.
Figure 5:
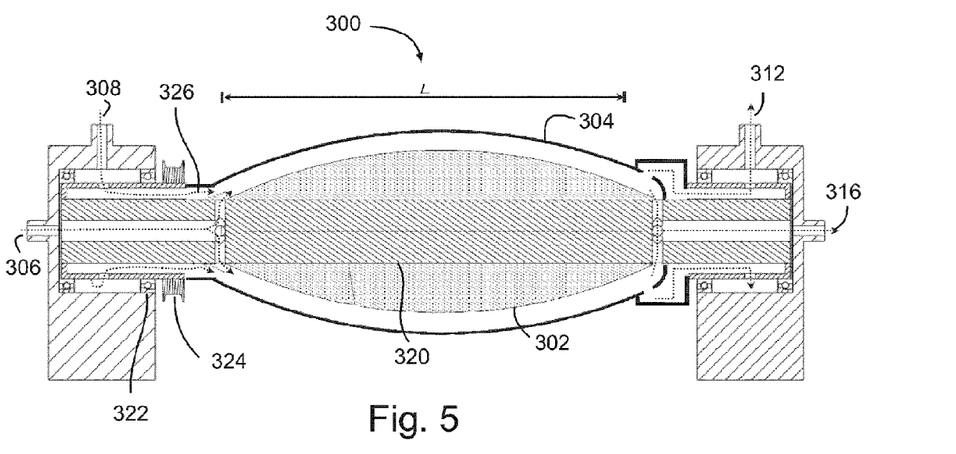

A classification system classifies the suspended particles according to their trajectories. In the embodiment shown particles are classified according to whether their trajectories bring them through sampling exit 114. The transfer function of the instrument (the distribution of particles that leave the classifier at any given operating condition) can be found by determining the trajectory of the particles. A sample flow 112 with flow rate $Q_s$ exits the classifier through sampling exit 114. In the embodiment shown, the sample flow is part of the sheath flow. The remainder of the sheath flow and the aerosol flow exit the classifier as exhaust flow 116. Defining $r_1$ as the outer radius of the inner cylinder, $r_2$ as the inner radius of the outer cylinder, $r_3$ as the outer radius of the aerosol flow, and $r_4$ as the inner radius of the sample flow, the largest particle (i.e., the largest $\tau$) that will pass through the classifier, exiting the classifier in the sample flow 112, will start at $r_{in}$=$r_1$ and will reach $r_2$ at the end of the classifier (z=L). Therefore, $$\tau_{max} = u_z\frac{\ln(r_2/r_1)}{\omega^2 L} = \frac{(Q_{sh}+Q_a)}{\pi(r_2^2-r_1^2)}\frac{\ln(r_2/r_1)}{\omega^2 L}. \tag{4}$$

The smallest particle that will be classified, $\tau_{min}$, will enter the classifier at $r_{in}$=$r_3$ and will reach $r_4$ at the end of the classifier. The radii $r_3$ and $r_4$ can be related to the radii $r_1$ and $r_2$, realizing that for uniform flow, $$u_z = \frac{Q_{sh}+Q_a}{\pi(r_2^2-r_1^2)} = \frac{Q_{sh}}{\pi(r_2^2-r_3^2)} = \frac{Q_s}{\pi(r_2^2-r_4^2)}. \tag{5}$$

Therefore, $$\tau_{min} = \frac{(Q_{sh}+Q_a)}{\pi\omega^2 L(r_2^2-r_1^2)}\ln\left(\frac{Q_{sh}+Q_a+Q_s(1-r_1^2/r_2^2)}{Q_{sh}+Q_a-Q_{sh}(1-r_1^2/r_2^2)}\right). \tag{6}$$

Particles with $\tau>\tau_{max}$ will intercept the outer cylinder wall before reaching the exit slit and will adhere to the cylinder surface, while particles with $\tau<\tau_{min}$ will flow past the exit slit and be carried out of the instrument with the exhaust flow. The particles adhere to the wall of the outer cylinder due to van der Waals forces (Friedlander, 2000) and will remain there until the cylinder is cleaned. (Like the DMA, under normal operating conditions and aerosol concentrations, the cylinder will only need to be cleaned once every few months.) Between the maximum and minimum relaxation times, only a fraction of the particles will be classified. A particle must migrate into the sample flow, defined by the sample streamline ($r_4 \le r < r_2$), by the time the particle has reached the end of the classifier. For particles with $\tau>\tau_{min}$, only particles with an initial radial position $r_c \le r < r_3$ will be classified, where $r_c$ is called the critical radius. The limiting trajectory for $\tau>\tau_{min}$ will be the particle that starts at $r_c$ and reaches $r_4$. Substituting this condition into Eq. 3 and solving for the aerosol fraction, $f_1$, that is classified reveals, $$f_1 = \frac{Q_{sh}+Q_a-\exp\left(\frac{-2\tau\omega^2 L\pi(r_2^2-r_1^2)}{Q_{sh}+Q_a}\right)(Q_{sh}+Q_a-Q_s(1-r_1^2/r_2^2))}{Q_a(1-r_1^2/r_2^2)} - \frac{Q_{sh}}{Q_a}. \tag{7}$$

Likewise, for particles with $\tau<\tau_{max}$, the particles starting at the critical radius, $r_c$, must reach $r_2$ by the end of the classifier. In this case the fraction of the aerosol, $f_2$, that is classified is, $$f_2 = \frac{Q_{sh}+Q_a}{Q_a}\left(1-\frac{1-\exp\left(\frac{-2\tau\omega^2 L\pi(r_2^2-r_1^2)}{Q_{sh}+Q_a}\right)}{1-r_1^2/r_2^2}\right). \tag{8}$$

Furthermore, if the sample flow rate is smaller than the aerosol flow rate, then the transfer function cannot be larger than, $f_3$=$Q_s/Q_a$.

The transfer function, $\Omega$, will be the minimum of these three fractions or one. Therefore, the transfer function can be expressed as, $\Omega=\max[0,\min(f_1,f_2,f_3,1)]$.

The normalized transfer function is shown in FIG. 3A, where the normalized particle relaxation time is defined as $\tau/\tau^*$. The value $\tau^*$ is the particle relaxation time at the centre of the transfer function and is defined as $\tau^*=(\tau_{max}+\tau_{min})/2$. The half-width of the transfer function is defined as, $\Delta\tau=(\tau_{max}-\tau_{min})/2$.

It can be shown, that when the gap between the cylinders is small and $Q_a$=$Q_s$, then the relative width of the transfer function, $\Delta\tau/\tau^*$, is Just the ratio of the aerosol to sheath flow rates, $\Delta\tau/\tau^*=Q_a/Q_{sh}$. To produce a highly monodisperse aerosol this ratio should approximately be in the range of 0.05 to 0.1.

As an example some sample dimensions and operating conditions that are well suited for most applications are: $r_2$=37 mm, $r_1$=35 mm, L=200 mm, $Q_{sh}$=3 L/min, and $Q_a$=$Q_s$=0.3 L/min. In general, it is beneficial to keep the gap between the cylinders relatively small (i.e. $(r_2-r_1) \ll r_1$), as smaller gaps increase the height of the transfer function. During operation the flow rates maybe changed to vary the width of the transfer function as desired as long as the flow remains laminar. An example of a transfer function of the APC is shown in FIG. 3B using the given dimensions. In this example, when the rotational speed is 5650 rpm the centre of the non-diffusion transfer function will be at $d_{ae}^*$=100 nm, with the minimum and maximum sizes classified at 92 nm and 108 nm, respectively. A more complicated model was also developed which accounts for the effects due to particle diffusion within the classification region. The diffusion transfer function is also shown in FIG. 3*b* and it shows that the transfer function becomes broader and shorter when diffusion is included. This affect will become more prevalent for smaller particle sizes.

Thus, this embodiment of the APC will produce a very narrow, or monodisperse, size distribution. Using these same dimensions, the APC would be able to classify particles over an extremely wide range for example 10 nm to 10 μm using rotational speeds ranging from 20,000 to 95 rpm and smaller particle sizes could be classified by using higher rotational speeds (by comparison the DMA is typically used over a range of approximately 2.5 to 1,000 nm).

It should be noted that the analysis used here is very similar to the proven theoretical analysis used in the DMA, with the exception that the APC has a centrifugal force instead of an electrostatic force to classify the particles. Therefore, we have a sound basis for predicting that this theoretical model of the APC will closely match experimental data once a prototype is developed.

The above description of the embodiment of the APC of FIG. 1 is just one way the instrument could be designed or configured. Other alternative designs can be envisioned depending on the application or requirements. These include: 1) the use of rotating channels instead of a continuous cylindrical section, 2) two cylinders rotating a slightly different rotational speeds, and 3) ways to measure aerosol size distributions.

Figure 6:
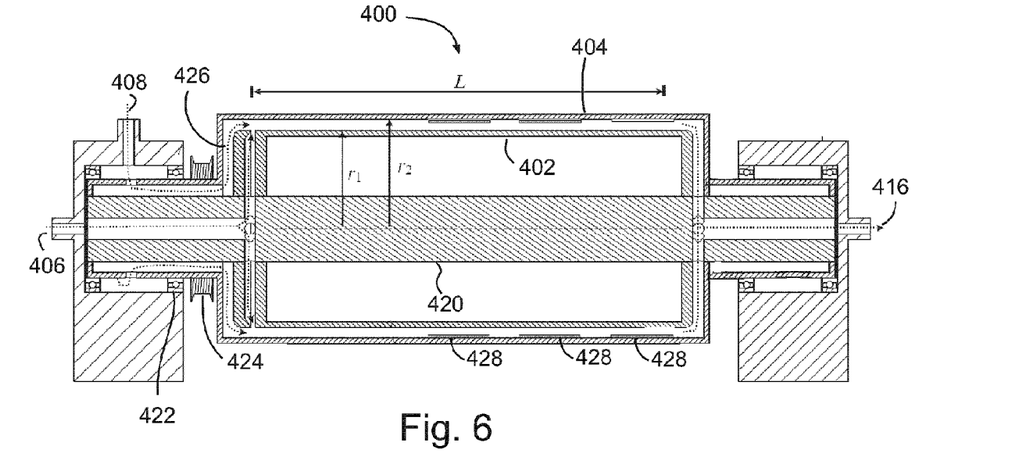
Figure 7A:
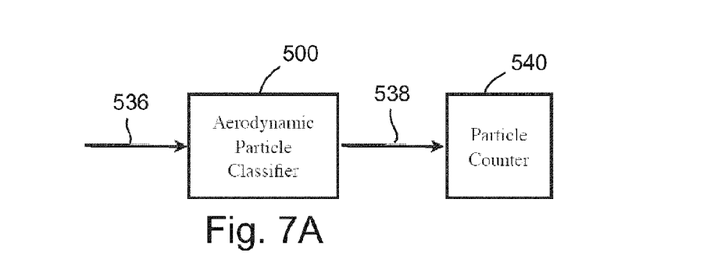
Figure 7B:
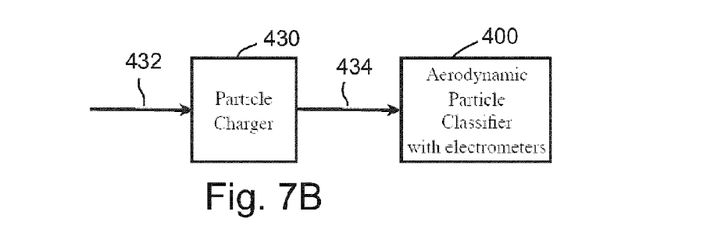

The embodiment of FIG. 1 uses concentric cylinders to classify the particles. However, other rotating geometries may also be used. For example, partial cylindrical sections such as sectors of a cylinder may be used as elements defining one or more carrier flow channels or other long channels attached to a rotating shaft may be used as the carrier flow channels. However, the analysis of the transfer function will change with these different geometries, where the cylindrical geometry is the simplest to analyze. Referring to FIG. 4, an APC 200 is shown with a rotating flow channel (multiple flow channels may be included around the central axis, but only one is shown in the figure). The flow channel may be defined by an inner partial cylindrical section 202 and an outer partial cylindrical section 204 although other shapes than partial cylindrical sections are possible. The embodiment may operate in a similar way as the embodiment of FIG. 1 except that the flow channel does not extend all the way around the central axis. In particular rotating shaft 220, bearings 222, pulley 224, sheath flow 208, aerosol flow 206, initial flow channel 226, sample flow 212 and exhaust flow 216 may be similar to their counterparts of FIG. 1 and cooperate similarly, except that the portions of the sheath flow and sample flow within the rotating parts of the classifier may not extend all the way around the central axis. Referring to FIG. 5, an APC 300 is shown with a flow channel defined by an inner surface 302 and an outer surface 304 which are not cylinders. The surfaces may be surfaces of revolution. However, it would also be possible to use different shapes including partial surfaces of revolution that extend only part of the way around the central axis, as in FIG. 4. Further shapes other than partial surfaces of revolution may also be used. The embodiment shown in FIG. 5 may operate in a similar way as the embodiment of FIG. 1 except for the different shape of the flow channel. In particular, rotating shaft 320, bearings 322, pulley 324, sheath flow 308, aerosol flow 306, initial flow channel 326, sample flow 312 and exhaust flow 316 may be similar to their counterparts of FIG. 1 and cooperate similarly, except where a different shape is appropriate to accommodate the shape of the flow channel.

In the analysis relating to FIGS. 1 and 2 it was assumed that the cylinders were rotating at the same rotational speed. However, cylinders rotating at slightly different speeds can also be used. In this case it would be preferable to rotate the inner cylinder slightly faster than the outer cylinder. When this is done, and the speed difference is large enough, the centrifugal force will decrease as its radial position increases. This causes the particle trajectories in the classifier to slightly 'converge' near the end of the classifier, resulting in a higher transfer function. A similar method is used in the Couette CPMA to improve its transfer function and it is the key difference between it and the APM. However, as shown in the example above (FIG. 3B) the peak of the transfer function without the speed difference is already 0.95, therefore the added complexity of rotating the cylinders at slightly different speeds is mostly likely not worth the slight improvement in transfer function. If different rotational speeds are used it should be noted that the speed ratio must satisfy the Rayleigh criterion (i.e., it must not be the case that $(r_1/r_2)^2>\omega_2/\omega_1$) beyond which the flow becomes unstable, thereby disturbing the classification of the particles.

Thirdly, the above description describes how the APC can be used to produce a monodisperse aerosol based on the particle's aerodynamic diameter, much like how a DMA is used to produce a quasi-monodisperse aerosol based on the particle's electrical mobility diameter. DMA's are often combined with a condensation particle counter (CPC) to measure the number concentration of the quasi-monodisperse aerosol. Typically, the voltage controlling the electrostatic field in the DMA is 'scanned' over the range of the instrument, and by completing a data inversion of the CPC data, the size distribution of the aerosol can be determined. This combination of DMA and CPC is normally called, a Scanning Mobility Particle Sizer (SMPS). The same method can be employed by combining the APC with a CPC, or any other particle counting device, and by continuously 'scanning' the rotational speed or intermittently stepping the rotational speed. That is, a particle counter could be placed in or connected to the particle classification system or the outlet of the particle classification system in order to detect the concentration of particles of an aerodynamic diameter or other derived metric allowing them to reach the particle counter; the acceleration provided to the flow could be varied continuously or in steps, the aerodynamic diameter (or other metric related to the aerodynamic diameter) required to reach the particle counter changing with the acceleration provided to the flow, so that the particle counter measures a spectrum of aerodynamic diameter (or other metric related to the aerodynamic diameter) versus concentration as the acceleration provided to the flow varies. Referring to FIG. 7A, an aerodynamic classifier 500, which may be of any of the embodiments described above, is shown with a particle counter 540. An initial aerosol flow 536 enters the classifier which acts on the aerosol flow to produce a classified flow 538 containing a selected portion of the aerosol particles present in the initial aerosol flow. The classified flow may be for example a sampling flow. The particle counter may be for example a condensation particle counter. The embodiment shown in FIG. 7A may include embodiments used to measure a spectrum of aerodynamic diameter versus concentration or other embodiments.

Another way the APC can be used to measure aerosol size distributions is by eliminating the aerosol exit slit and placing in the flow channel one or more detectors at which the particles may impact depending on their trajectory and measuring the number of particles impacting the one or more detectors. In an embodiment a detector may comprise a conductor connected to an electrometer circuit, for example in an annular embodiment, the detector may comprise a conducting ring connected to an electrometer. The ring may be electrically isolated from both the remainder of the surface defining the flow channel and any other detection rings which may be present. The detectors may be situated at different axial locations along the outermost surface of the flow channel. Referring to FIG. 6, an APC 400 is shown having detectors 428 located in the flow channel at which particles may impact depending on their trajectory. In the embodiment shown the flow channel is defined by cylinders as in FIG. 1, although other shapes would also work. In this embodiment the detectors may be rings, electrically connected to electrometer circuits, extending around the inside of the outer cylinder. No sampling exit is necessary to classify particles when detectors are used to detect impacting particles, although the detectors could also be used in embodiments with a sampling exit. The embodiment shown in FIG. 6 may otherwise operate similarly to the embodiment of FIG. 1, in particular, the rotating shaft 420, bearings 422, pulley 424, sheath flow 408, aerosol flow 406, initial flow channel 426, and exhaust flow 416 may be similar to their counterparts of FIG. 1 and cooperate similarly, except that the articles of the aerosol flow are charged. In this system, the particles to be measured would be charged (most likely with a corona discharge-type charger or any other particle charging method, see Hinds, *Aerosol Technology*, Wiley, 1999). The charged particles would move down the classification section and impact the electrometer rings on the outer cylinder, thereby causing a measurable current in the electrometer ring, where the current is proportional to the number concentration of particles impacting the electrometer. Larger particles would impact the electrometer rings near the aerosol entrance and smaller particles would impact the rings near the aerosol exit. Referring to FIG. 7B an APC 400 with electrometers, such as for example the APC shown in FIG. 6, is shown with a particle charger 430. An uncharged aerosol flow 432 enters the particle charger 430 to produce a charged aerosol flow 434 comprising charged aerosol particles. The APC 400 operates on the charged aerosol flow 434 to classify the charged aerosol particles. By using a data inversion routine, the aerosol size distribution can be determined. Similar techniques have been used in DMA-like instruments like the differential mobility spectrometer (Reavell et al., A fast response particulate spectrometer for combustion aerosols. *Society of Automotive Engineers,* 2002) and the engine exhaust particle sizer (Johnson et al., An engine exhaust particle sizer spectrometer for transient emission particle measurements. *Society of Automotive Engineers,* 2004); where electrometer rings have been placed inside a DMA-like classification column.

Thus the applicant has devised a new instrument, called the Aerodynamic Particle Classifier (APC). As indicated, a detailed theoretical model has been developed for the instrument. The model shows the instrument can have excellent classification properties (i.e. wide range, high resolution, and high penetration efficiency) without requiring particle charging. This results in an instrument that in an embodiment can produce a true monodisperse aerosol without classifying multiply-charged particles like the DMA, APM, or CPMA. An APC could be combined in series with a DMA or CPMA in order to measure other important particle properties including: mobility diameter, particle mass, effective density, fractal-like dimension, and dynamic shape factor.

Immaterial modifications may be made to the embodiments described here without departing from what is covered by the claims.

In the claims, the word "comprising" is used in its inclusive sense and does not exclude other elements being present. The indefinite article "a" before a claim feature does not exclude more than one of the feature being present. Each one of the individual features described here may be used in one or more embodiments and is not, by virtue only of being described here, to be construed as essential to all embodiments as defined by the claims.

The embodiments of the invention in which an exclusive property or privilege is claimed are defined as follows:

1. A method of classification of particles suspended in a fluid comprising the steps of:
    providing a substantially laminar carrier flow of a fluid where the fluid velocity has at least a rotational component causing centripetal acceleration and a translation component parallel to the axis of rotation;
    supplying particles into suspension in the carrier flow,
    in which the particles follow trajectories determined by the centripetal acceleration and drag on the particles caused by the fluid without any substantial influence from any electrostatic force; and
    classifying the particles according to the trajectories of the particles, in which the step of classifying particles according to the trajectory of the particles comprises splitting the carrier flow into two or more flows.

2. The method of claim 1 in which the fluid is a gas and the particles are aerosol particles.

3. The method of claim 2 in which the fluid is air.

4. The method of claim 1 in which the step of supplying particles into suspension in the carrier flow comprises merging a flow of a fluid containing suspended particles into the carrier flow.

5. The method of claim 1 in which the step of classifying the particles according to the trajectory of the particles comprises supplying a surface at which particles may impact depending on their trajectory.

6. The method of claim 5 further comprising the steps of varying the acceleration provided to the flow and measuring the concentration of particles in a continuing flow in a downstream direction from the surface as the acceleration provided to the flow is varied.

7. The method of claim 1 further comprising the steps of varying the acceleration provided to the flow and measuring the concentration of particles in at least one of the two or more flows as the acceleration provided to the flow is varied.

8. The method of claim 7 in which the measurement of concentration at varying acceleration is used to obtain a spectrum of concentration spectral density versus aerodynamic particle diameter or particle mass to drag ratio or equivalent metric.

9. The method of claim 1 in which the carrier flow is provided through a channel having an inner rotational surface and the particles are supplied into the carrier flow through the inner rotational surface.

10. The method of claim 1 in which the particles are classified within a range of particle sizes between a maximum size and a minimum size.

11. A method of classification of particles suspended in a fluid comprising the steps of:
    providing a substantially laminar carrier flow of a fluid where the fluid velocity has at least a rotational component causing centripetal acceleration and a translation component parallel to the axis of rotation,
    supplying particles into suspension in the carrier flow;
    in which the particles follow trajectories determined by the centripetal acceleration and drag on the particles caused by the fluid without any substantial influence from any electrostatic force; and
    classifying the particles according to the trajectories of the particles in which the step of classifying the particles comprises supplying one or more detectors at which the particles may impact depending on their trajectory and measuring the number of particles impacting the one or more detectors.

12. The method of claim 11 further comprising the step of charging the particles and in which the detectors are electrically conductive and are each connected to an electrometer circuit.

13. An apparatus for classifying particles suspended in a fluid, the apparatus comprising:

one or more elements defining a carrier flow channel or plurality of channels;

a source of a substantially laminar carrier fluid flow into the carrier flow channel or channels;

a source of particles connected to supply the particles into suspension in the carrier fluid in the carrier flow channel or channels;

a drive connected to rotate the elements defining the carrier flow channel or channels to supply an acceleration to the elements defining the flow channel or channels at an angle to the flow of fluid through the carrier flow channel or channels; and a classification system for classifying the suspended particles according to their trajectories when the suspended particles move with a component of their velocity parallel to the axis of the rotation, without any substantial influence from any electrostatic force, in which the classification system comprises elements defining a split of the carrier flow channel or channels into two or more channels.

14. The apparatus of claim 13 in which the carrier fluid is a gas and the particles are aerosol particles.

15. The apparatus of claim 14 in which the carrier fluid is air.

16. The apparatus of claim 14 in which the source of particles is supplied into the carrier flow channel by an opening substantially in the inner rotational surface of the carrier flow channel.

17. The apparatus of claim 13 which the one or more elements defining a carrier flow channel substantially form surfaces of rotation about a central rotational axis.

18. The apparatus of claim 13 in which the carrier flow channel is substantially cylindrical in shape.

19. The apparatus of claim 18 in which the elements defining the carrier flow channel are cylinders.

20. The apparatus of claim 13 in which one or more of the elements defining the carrier flow channel or channels substantially form sectors of surfaces of rotation about a central rotational axis.

21. The apparatus of claim 20 in which one or more of the elements defining the flow channel or flow channels are substantially shaped as sectors of a cylinder.

22. The apparatus of claim 13 in which the drive comprises a motor.

23. The apparatus of claim 13 in which the source of particles connected to supply the particles into suspension in the carrier fluid in the carrier flow channel or channels comprises elements defining a suspension flow channel or channels which intersects the carrier flow channel or channels, the suspension flow channel or channels being capable of directing a fluid containing suspended particles into the carrier flow channel or channels.

24. The apparatus of claim 13 in which the classification system comprises an outlet connected to or incorporating a particle detector, the drive having a variable rotation speed.

25. An apparatus for classifying particles suspended in a fluid, the apparatus comprising:

one or more elements defining a carrier flow channel or plurality of channels;

a source of a substantially laminar carrier fluid flow into the carrier flow channel or channels:

a source of particles connected to supply the particles into suspension in the carrier fluid in the carrier flow channel or channels:

a drive connected to rotate the elements defining the carrier flow channel or channels to supply an acceleration to the elements defining the flow channel or channels at an angle to the flow of fluid through the carrier flow channel or channels; and a classification system for classifying the suspended particles according to their trajectories when the suspended particles move with a component of their velocity parallel to the axis of the rotation, without any substantial influence from any electrostatic force in which the classification system comprises a surface of each carrier flow channel at which particles suspended in fluid in the carrier flow channel may impact depending on their trajectory, and the surface is a surface of a detector element.

26. The apparatus of claim 25 in which the surface is an element defining or partially defining the carrier flow channel.

27. The apparatus of claim 25 in which the source of particles comprises a charging means for charging the particles and the detector element comprises at least a conductive detector placed along the flow channel, the at least a conductive detector connected to an electrometer circuit.

28. The apparatus of claim 25 in which the classification system operates by classifying particles within a range of particle sizes between a maximum size and a minimum size.

* * * * *